United States Patent [19]

Turner et al.

[11] 4,261,356

[45] Apr. 14, 1981

[54] METHOD AND APPARATUS FOR CONTROLLING THE DISPENSING OF FLUID

[75] Inventors: Roger S. Turner; Charles R. Turner, both of Philadelphia, Pa.

[73] Assignee: Baxter Travenol Laboratories, Inc., Deerfield, Ill.

[21] Appl. No.: 953,861

[22] Filed: Oct. 23, 1978

Related U.S. Application Data

[62] Division of Ser. No. 732,946, Oct. 15, 1976, Pat. No. 4,121,584.

[51] Int. Cl.³ ............................................. A61M 5/00
[52] U.S. Cl. ................................. 128/214 R; 222/450; 222/207
[58] Field of Search ........... 128/214 R, 214 E, 214 F, 128/214 C, 214 Z, 227, DIG. 12, DIG. 13; 222/445, 450-452, 207

[56] References Cited

U.S. PATENT DOCUMENTS

| 2,726,019 | 12/1955 | Moran | 222/451 X |
| 2,895,653 | 7/1959 | Giepen | 222/45 Z |
| 3,314,371 | 4/1967 | Hopkinson | 222/450 X |
| 4,121,584 | 10/1978 | Turner et al. | 128/214 E |
| 4,126,132 | 11/1978 | Portner et al. | 128/214 F |

FOREIGN PATENT DOCUMENTS 744552 2/1956 United Kingdom .
1368566 10/1974 United Kingdom .

Primary Examiner—Dalton L. Truluck
Attorney, Agent, or Firm—Paul C. Flattery; John P. Kirby, Jr.; W. Garrettson Ellis

[57] ABSTRACT

A method is disclosed for controlling the dispensing of fluid from a source at a hydrostatic pressure involving the sequential measuring and dispensing of predetermined volumetric increments of fluid from the source of fluid during different ones of a series of time intervals. Apparatus is also provided for controlling the dispensing of fluid, including metering means for receiving a predetermined increment of fluid and for emptying the predetermined increment of fluid, conduit means for delivering fluid from a source of fluid to the metering means, and control means for actuating the metering means between a condition for receiving one predetermined increment of fluid and a condition for emptying the predetermined increment of fluid.

18 Claims, 20 Drawing Figures

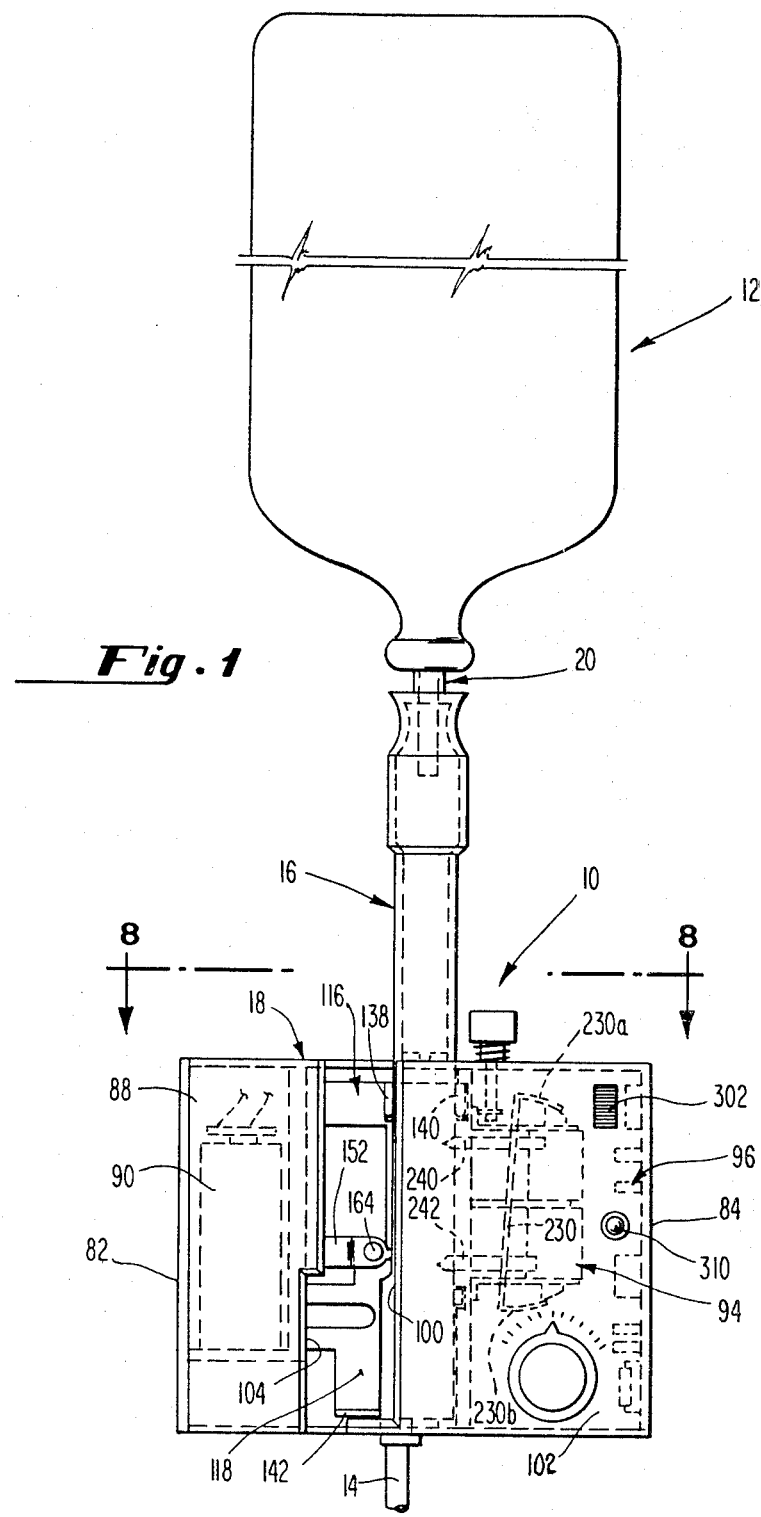

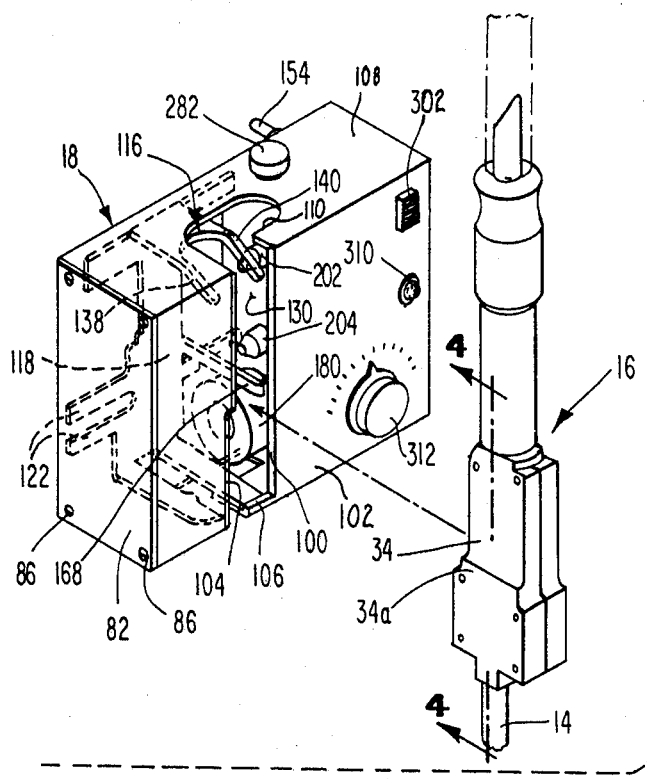
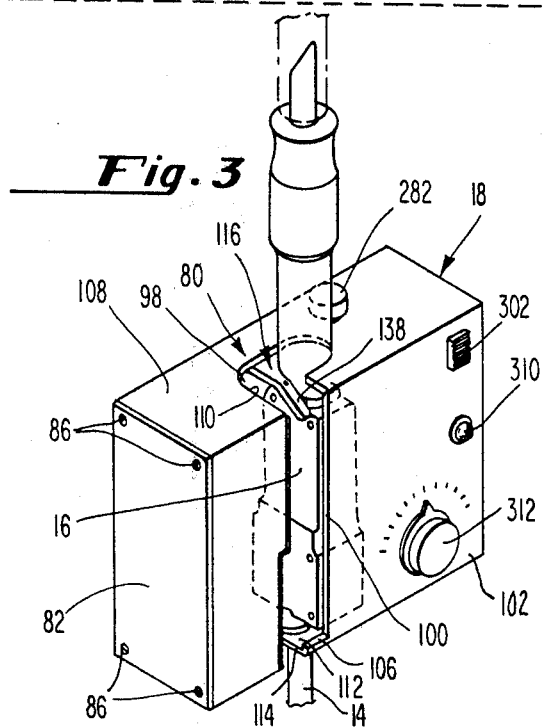
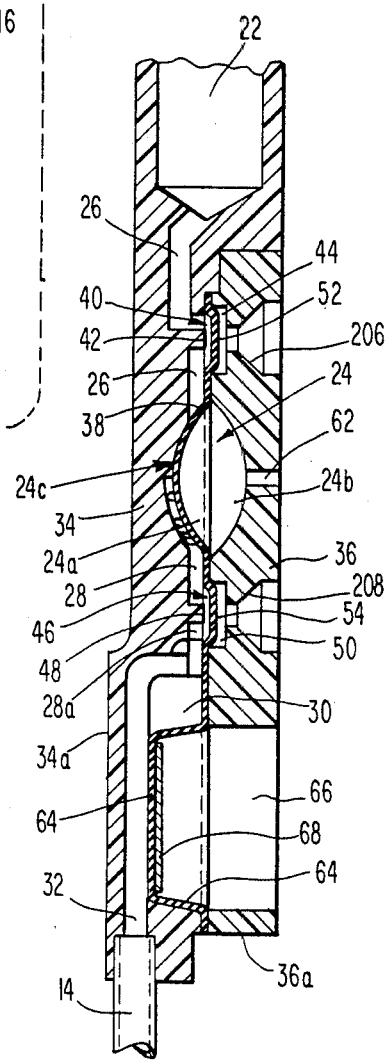

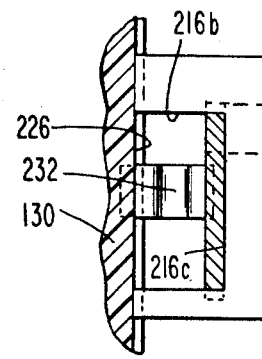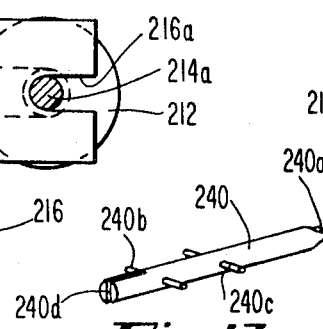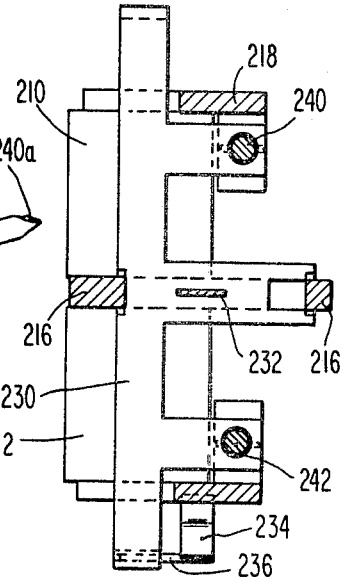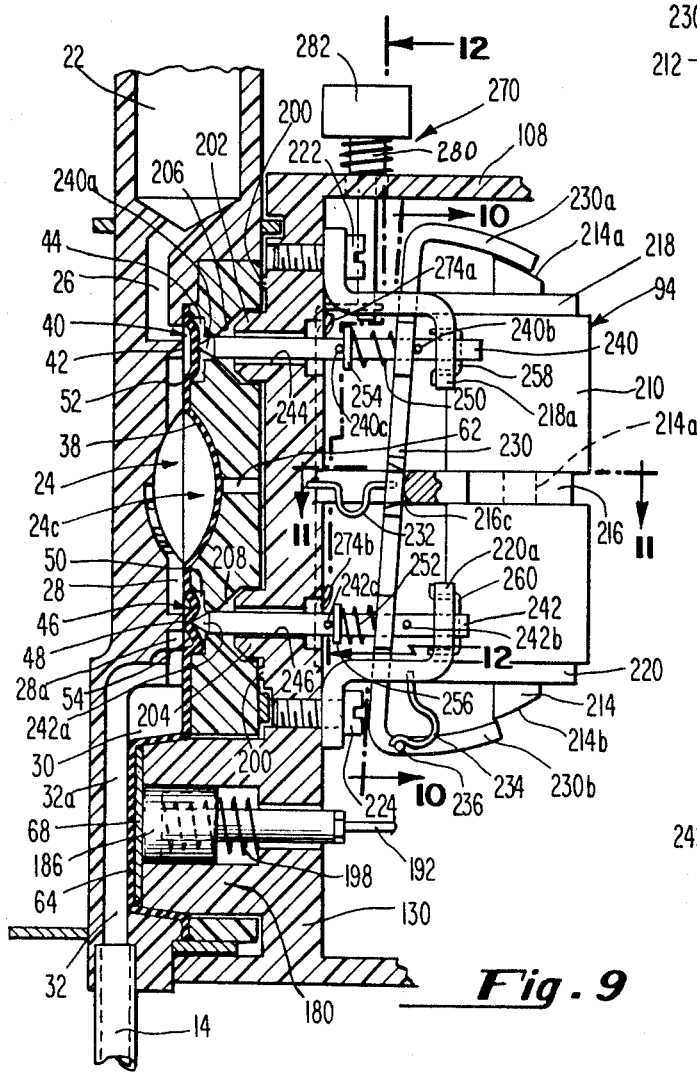

METHOD AND APPARATUS FOR CONTROLLING THE DISPENSING OF FLUID

This is a division of application Ser. No. 732,946, filed Oct. 15, 1976, now U.S. Pat. No. 4,121,584.

BACKGROUND OF THE INVENTION

This invention relates to a method and apparatus for controlling the dispensing of fluid, and more particularly, to a means for controlling the intravenous administration of a desired dose of fluid into a body.

The present invention is concerned with controlling the dispensing of fluid and is primarily concerned with the intravenous administration of a desired dose of fluid into the body of a patient. In the prior art, apparatus used for the intravenous administration of fluid have been generally of two basic varieties. The most common intravenous administration device is of the gravity flow type in which the rate of delivery of fluid is adjusted by means of a variable restriction. In such gravity flow systems, the variable restriction is usually provided by a clamping device that deforms a resilient fluid delivery tube connected to the hypodermic needle through which the fluid is introduced into the vascular system of the patient. The gravity flow types of devices may vary widely in cost and in the manner and complexity for controlling the flow rate of the fluid delivered to the patient.

It has been found that such gravity flow devices employing a variable restriction are incapable of reliable and uniform operation due to a number of factors, such as, the tendency of the plastic delivery tube to be subject to delayed plastic flow under stress, the variations in the hydrostatic pressure from the volume of fluid to be administered, variations in fluid viscosity, and changes in physical position and vascular pressure of the patient that may occur during administration of a quantity of fluid. In the gravity flow types of devices, the adjustment of the variable restriction governing the flow rate may be required to be performed manually, which is time consuming and subject to erroneous adjustment. Also, it is desirable for a doctor or nurse to frequently check the flow rate in administration of fluid in such devices to make sure that it is properly regulated. Moreover, a possible serious problem may occur in use of these types of devices when a complete stoppage of flow of fluid takes place, if the device is unattended at the time of exhaustion of the fluid. The unattended stoppage of flow of fluid at the needle in the patient may result in a blood clot which may cause a dangerous condition for the patient.

The other common variety of intravenous administration device is of the pump type which was designed to overcome various disadvantages of the gravity flow types of intravenous administration devices. Many different and complicated arrangements have been developed for regulating the pumping action and the quantity of fluid discharged. In the prior art, much design effort has been exerted to overcome the inherent capacity of the pump to force air into the patient with possible fatal consequences. The pump type of intravenous administration device has tended to be expensive, cumbersome, and complicated in structure. Further, these devices have been dependent upon a source of power greater than can be reliably and economically supplied by a battery. Various clinical reasons exist for avoiding the use of alternating current sources of power with intravenous administration devices, such as, electro-magnetic interference created by the power supply interfering with sensitive clinical devices and electrical impulses from the electrical systems for the pump devices being transmitted through intravenous fluid, which may be electrically conductive, to patients having sensitive heart conditions.

Accordingly, it is an objective of the present invention to provide an intravenous administration apparatus which is inexpensive and simple to operate while administering a desired dose of fluid in an accurately controlled manner. In order to accomplish this objective, it is desirable to provide a method and associated apparatus for intravenous administration of fluid at an accurately controlled rate irrespective of variables, such as, the level of fluid in the source, the venous pressure of the patient, and the viscosity of the fluid. Furthermore, it is desirable to provide an intravenous administration apparatus which enables automatic and progressive reduction of the rate of administration of the fluid at or near the time the desired dose has been administered and before complete exhaustion of the fluid in the administration apparatus so that air is not injected into the patient and blood clotting at the point of administration is prevented.

It is desirable to provide an intravenous administration apparatus which is small in size, light in weight, easily portable, and rugged in design. It is also desirable to provide such apparatus which includes a reusable timer capable of a long expectancy of use and a small, portable, replaceable power supply capable of supplying power to the apparatus. It is further highly desirable to provide an intravenous administration apparatus in which the parts of the apparatus through which the fluid passes is provided by a disposable unit, which is replaced after each use for easily maintaining the apparatus in a sterile condition. Moreover, it is desirable to provide an intravenous administration apparatus in which the parts of the apparatus are adapted to cooperate together in operative relationship only when the apparatus is properly assembled and conditioned for safe administration of fluid and provide such an apparatus which minimizes the likelihood of error by the person responsible for performing the intravenous administration of fluid to the patient.

SUMMARY OF THE INVENTION

In accordance with the present invention, a new and improved method and apparatus has been provided with novel features which cooperate to enable an economical, accurately controlled and reliable arrangement for intravenous administration of a volume of fluid. Accordingly, these and other objects are achieved by providing a novel method for controlling the dispensing of a fluid from a source at a hydrostatic pressure, which comprises the procedure of measuring the fluid from the source into predetermined volumetric increments for dispensing the fluid, providing time intervals for measuring and dispensing of the predetermined volumetric increments of fluid, and then sequentially metering each of the predetermined volumetric increments of fluid during different ones of the time intervals. In accordance with the preferred process of dispensing the fluid, the predetermined volumetric increments are released from the source of fluid by providing a receptacle having a size of the predetermined volumetric increment and the receptacle is filled with fluid by gravity flow from the source of fluid and then the fluid is emptied from the receptacle for administration during each of the time intervals.

The preferred apparatus employed in accordance with the present invention for controlling the dispensing of fluid at a hydrostatic pressure includes metering means for receiving a predetermined increment of fluid and for emptying the predetermined increment of fluid. In addition, the apparatus has conduit means for delivering fluid to the metering means from a source of fluid having a supply of predetermined increments of fluid, and control means for actuating the metering means between a condition for receiving a predetermined increment of fluid and a condition for emptying the predetermined increment of fluid.

The fluid from the source is dispensed through the metering means by the metering means sequentially receiving and emptying each of the predetermined increments of fluid. For this purpose, the metering means has a metering chamber and the apparatus further includes valve means for regulating the receiving and emptying of fluid by the metering chamber. The valve means is preferably provided by an inlet valve connected with one part of the metering chamber and an outlet valve connected with another part of the metering chamber, the inlet and outlet valves being operable in response to actuation from the control means to permit the metering chamber to receive and empty the predetermined increments of fluid. The control means includes timer means for sequentially providing a time interval in which the inlet valve permits passage of fluid into the metering chamber and the outlet valve prevents passage of fluid, and the timer means provides another time interval in which the inlet valve prevents passage of fluid into the metering chamber and the outlet valve permits passage of the predetermined increment of fluid from the metering chamber.

In one form of the invention, the control means or unit includes releasable fastening means, which may be provided by retaining and positioning means, cooperating with the metering means or unit to hold the metering unit in fixed operative relationship with the control unit for having the valve means responsive to the control unit. Also, preferably, the metering unit includes hydraulic means with a fluid chamber receiving fluid from the metering chamber for having fluid in the fluid chamber move into the metering chamber to cause air in the metering chamber to be expelled through the conduit means, when the retaining and positioning means moves the metering unit into the fixed operative relationship. In this arrangement, the control unit includes actuating means cooperable with the hydraulic means to actuate the hydraulic means to move fluid in the fluid chamber into the metering chamber when the retaining means couples the components together in operative relationship. In order to assure that air has been expelled from the metering chamber when the apparatus is to be operated, the control unit further includes interlock sensor means for sensing fluid in the fluid chamber and preventing the retaining and positioning means from moving the metering unit into the fixed operative relationship with the control unit, when a predetermined volume of fluid is not present in the fluid chamber for being moved into the metering chamber to purge air from the metering chamber.

In still a further arrangement of the present invention, the apparatus includes a reservoir chamber adapted to receive a portion of the increments of fluid from the source of fluid and to hold the fluid at a second hydrostatic pressure, and inlet means connects the reservoir chamber with the metering chamber. When the source of fluid has been emptied in this arrangement, the second hydrostatic pressure of the fluid in the reservoir chamber is only sufficient to have the metering chamber receive a portion of a predetermined increment of fluid from the reservoir chamber in the time interval provided, so that continued metering of fluid to the patient is provided at a reduced rate to prevent blood clotting at the hypodermic needle in the patient. In this manner, a longer time is allowed for the person responsible for administering the intravenous dose to return to the patient and remove the apparatus at or after the time that the desired dose has been administered to the patient.

The arrangement of the metering unit and control unit in accordance with the present invention is such that, in dispensing the fluid, the fluid passes through the metering unit without contacting the control unit. Hence, the control unit does not have to be maintained in a sterile or uncontaminated condition. The control unit will be reused and only the metering unit, which is made as a disposable item, will be discarded after having been used once. Thereafter, upon the next desired use of the apparatus, a new metering unit is used in cooperation with the control unit. It should be appreciated that the intravenous administration apparatus of the present invention can be used for many intravenous administrations of fluid and only requires replacement of the inexpensive metering unit between uses. Further, the features of the present invention minimize the likelihood or error in administration of fluid by the person responsible for using the apparatus and has many safety features to prevent the occurrence of dangerous conditions to the patient during the intravenous administration of the fluid.

For a better understanding of these and other features and advantages of the present invention, reference is made to the following drawings, in which:

FIG. 1 is an elevational view showing an apparatus for controlling the dispensing of fluid embodying the present invention connected with a container of fluid;

FIG. 2 is a perspective view of the control unit and metering unit of FIG. 1 and showing the units prior to being fastened together;

FIG. 3 is a perspective view of the control unit and metering unit of FIG. 2 but showing the units fastened together in operative relationship;

FIG. 4 is an enlarged fragmentary sectional view taken along line 4—4 of FIG. 2;

FIG. 9 is a fragmentary sectional view taken along line 9—9 of FIG. 8;

FIG. 10 is a sectional view taken along line 10—10 of FIG. 9;

FIG. 11 is a fragmentary sectional view taken along line 11—11 of FIG. 9;

FIG. 12 is a fragmentary sectional view taken along line 12—12 of FIG. 9;

FIG. 13 is a reduced-dimension perspective view of one of the valve actuator pins of FIG. 9;

DESCRIPTION OF THE PREFERRED EMBODIMENTS

Figure 5:
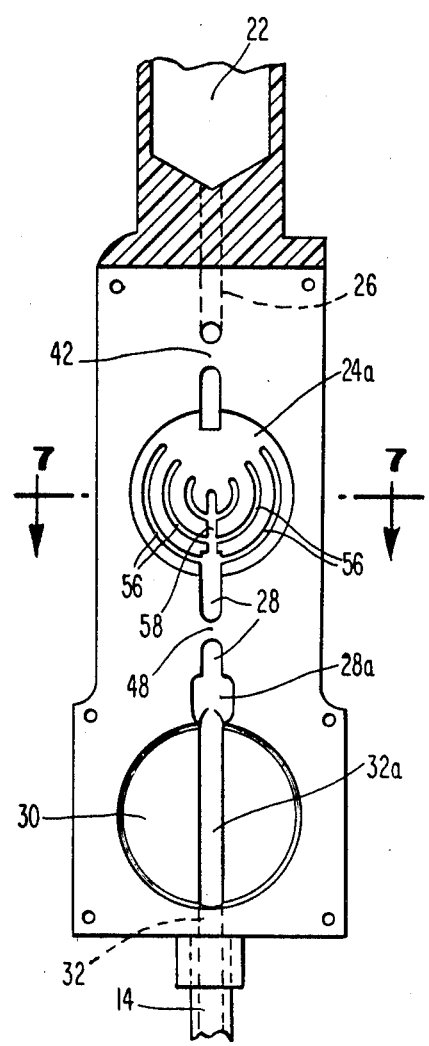
FIG. 5 is a fragmentary side elevational view of the metering unit of FIG. 4 but showing the cover panel of the metering unit and the metering unit diaphragm removed.

The apparatus of the present invention may be used in many different applications for controlling the rate of flow of fluid from a source of fluid. The use of the present apparatus is not limited to administration of fluid from a fixed volume or quantity of fluid. The apparatus can be used, for example, in proportioning the mixture of two or more ingredients in a mixing or processing operation where one or more apparatus in accordance with the present invention is employed. While the apparatus for controlling the dispensing of fluid at a hydrostatic pressure in accordance with the present invention may be used for dispensing fluid in a wide variety of applications, the apparatus will be described in use in intravenous administration of a volume of fluid as a dose injected in a host, which may be an animal or human and will be referred to hereinafter as a patient. The apparatus of the present invention is particularly useful in this latter application where an accurately controlled rate of administration of a fluid is required and safety in operation of the apparatus is important.

Referring now to the embodiment of the invention illustrated in FIG. 1, the invention is shown in use for intravenous administration of fluid to a patient (not shown). The intravenous administration apparatus generally designated 10 for controlling the dispensing of fluid at a hydrostatic pressure to a patient is connected to a source of fluid 12, which is shown as a fluid storage bottle or container adapted to be supported above the apparatus 10, which in turn is preferably positioned a distance above the point of application of the fluid into the patient. The fluid may be administered into the patient by a hypodermic needle (not shown) inserted into the vascular system of the patient and connected to the output of the apparatus 10 by suitable, flexible tubing 14. It is preferred for the apparatus 10 to be suspended at a height of at least thirty inches above the point of application to the patient to cause fluid to flow from the container through the apparatus to the patient by gravity flow. The hydrostatic pressure of the fluid as referred to herein indicates the force or pressure that the fluid exerts as it flows into the apparatus 10, and in the application of the apparatus in FIG. 1, the hydrostatic pressure corresponds to the force or pressure of gravity. Of course, in intravenous administration, the term fluid is used to indicate a liquid.

There is shown in FIGS. 1-3 the apparatus 10 comprising a metering means or unit generally designated 16 and a control means or unit generally designated 18. The metering unit 16 and control unit 18, which are shown separated in FIG. 2, are adapted to interfit together, as indicated in FIGS. 1 and 3, with the control unit having releasable fastening means cooperating with the metering unit for holding the metering unit in fixed operative relationship to the control unit 18. The metering unit and control unit are adapted to cooperate together in operative relationship such that in dispensing the fluid by the apparatus, fluid passes through the metering unit 16 without contacting the control unit 18. More particularly, the metering unit 16 is provided for receiving predetermined increments of fluid from fluid supply bottle or container 12 through inlet tube or conduit means 20 and for emptying the predetermined increments of fluid through outlet tube or conduit means 14 to the patient. Control unit 18 is provided for actuating the metering unit between a condition for receiving a predetermined increment of fluid and a condition for emptying the predetermined increment of fluid in a sequential manner.

According to the preferred process of use of the invention, the fluid from the supply container is measured into predetermined volumetric increments in the metering unit and time intervals are set for measuring and dispensing of the predetermined volumetric increments of fluid through the metering unit. In this procedure, the invention provides sequential measuring and dispensing of each of the predetermined volumetric increments of fluid during different ones of the time intervals. The measuring and dispensing of the volumetric increments of fluid is referred to herein as metering of fluid. In this arrangement, the metering unit 16 is provided with a receptacle or metering chamber having a size of the predetermined volumetric increment and the receptacle is filled with fluid by gravity flow from the fluid supply container and then the receptacle is emptied of fluid for intravenous administration into the body during each of the time intervals, as will be explained more fully hereinafter.

The metering unit 16 for receiving the fluid from the container 12 and emptying the fluid in predetermined volumetric increments to the patient is shown most clearly in FIGS. 4, 5, and 9. Metering unit 16 includes a reservoir or drip chamber 22, metering chamber 24, inlet means or conduit 26 connected between drip chamber 22 and metering chamber 24, and outlet means or conduit 28 extending from the metering chamber to an enlarged fluid chamber 30. The fluid from fluid chamber 30 passes through outlet passage 32 into tube 14, which is received in an increased diameter recessed encircling passage 32. The outlet conduit 28 also communicates directly with outlet passage 32 by means of a channel or groove 32a formed in body portion 34 and extending through fluid chamber 30, as shown in FIGS. 4, 5, and 9. Metering unit 16 is preferably made of a rigid plastic material, such as polystyrene, and includes a main body member or portion 34 and a cover portion or panel 36, which divides the metering unit into two parts in forming a portion of inlet conduit 26, metering chamber 24, outlet conduit 28, and fluid chamber 30, as shown most clearly in FIGS. 4 and 9. Further, a resilient metering diaphragm 38 of resilient plastic material, such as polyurethane, is captured between the metering unit body portion 34 and the metering unit cover panel 36. The metering unit body portion 34 and metering unit cover panel 36 with diaphragm 38 captured therebetween are preferably joined together by ultrasonic or high-frequency induction bonding, or may be joined together by any suitable epoxy or bonding compound or by screws.

Figure 6:
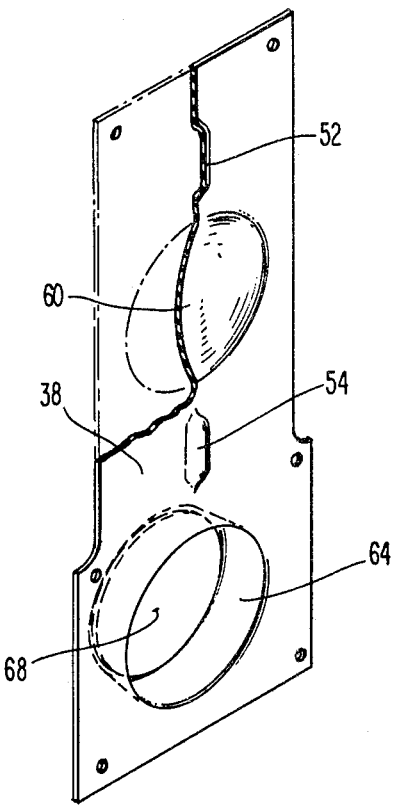
FIG. 6 is a fragmentary perspective view of the metering unit diaphragm of FIG. 4.
Figure 7:
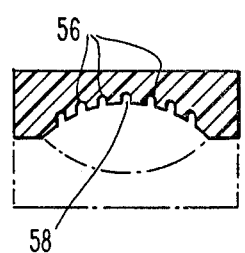
FIG. 7 is a sectional view taken along line 7—7 of FIG. 5.

As shown most clearly in FIGS. 4, 5, and 9, the inlet conduit 26 has inlet valve means generally designated 40 therein and is a serpentine-shaped passage around raised portion or projection 42, which closes inlet conduit 26 in body portion 34 and forms a valve face. Cavity 44 formed as a recess in cover panel 36 provides a valve cavity and facilitates flow of fluid around projection 42 in inlet conduit 26. Similarly, outlet conduit 28 has outlet valve means generally designated 46 therein and is a serpentine-shaped passage around raised portion or projection 48, which closes outlet conduit 28 in body portion 34 and forms a valve face. Cavity 50 formed as a recess in cover panel 36 provides a valve cavity and facilitates flow of fluid around projection 48 in outlet conduit 28. In this arrangement, the diaphragm 38, as shown in FIG. 6, has a protrusion 52, which provides a resilient valve element received in valve cavity 44 and a second protrusion 54, which provides a resilient valve element received in valve cavity 50. The resilient valve elements 52 and 54 are normally in the position shown in FIG. 4 which have the inlet conduit 26 and outlet conduit 28, respectively, in a condition to permit fluid to flow therethrough. The resilient valve elements 52 and 54 are actuated from positions in which the inlet and outlet conduits are open and to positions in which the inlet and outlet conduits are alternately closed by valve actuator means of the control unit, as will be explained more fully hereinafter.

The metering chamber 24 of the metering unit 16 is formed by two opposed arcuate-shaped domes or cavities 24a and 24b in body portion 34 and cover panel 36, respectively. There is provided in arcuate-shaped dome 24a of metering chamber 24 a series of arcuate-shaped recesses 56 communicating with drain passage 58, which in turn communicates with outlet conduit 28. The recesses 56 and passage 58 are provided to facilitate complete emptying of fluid from the metering chamber when it is desired to empty the fluid from the metering chamber. In this arrangement, the diaphragm 38 extends through the metering chamber 24 and is provided with an arcuate-shaped dome 60, which generally conforms to the shape of arcuate-shaped dome 24a of the metering chamber in its normal condition, as shown in FIGS. 4 and 6. The arcuate-shaped dome 60 of the diaphragm provides a movable wall and also conforms to the shape of arcuate-shaped dome 24b of the metering chamber. The diaphragm wall 60 is moved by the force of fluid flowing into the metering chamber to be adjacent dome surface 24b, when the metering chamber is filled with fluid as shown in FIG. 9. A cylindrical air passage 62 is provided through cover panel 36 communicating with dome portion 24b of the metering chamber to permit the movement of air from and into the metering chamber behind movable diaphragm wall 60 as the diaphragm wall 60 moves between a position in which the metering chamber is emptied, as shown in FIG. 4, and a position in which the metering chamber is filled with fluid as shown in FIG. 9.

It will be appreciated that, as the diaphragm wall 60 moves back and forth for fluid to be received and emptied from the metering chamber 24, fluid only contacts one side of the diaphragm wall 60 and the area between metering chamber dome 24a and diaphragm wall 60 defines the active fluid receiving and dispensing portion, generally designated 24c in FIG. 4, of the metering chamber. Although the size of the active fluid portion 24c of the metering chamber 24 varies in size as fluid fills and is emptied from the metering chamber, for convenience in describing the apparatus and its operation, the active fluid portion 24c of the metering chamber 24 will merely be referred to as the metering chamber 24 for receiving and emptying fluid. In this arrangement, the diaphragm wall 60 provides movable means in the metering chamber for varying the size of the metering chamber so that the metering unit is operable in receiving and draining the increments of fluid without air passing through the metering chamber.

In the embodiment of the diaphragm 38 illustrated in the drawings, the pressure to move the diaphragm wall 60 from the position shown in FIG. 4 to the position shown in FIG. 9 is as little as one half inch or less of water head. Therefore, there is always more than adequate hydrostatic pressure to cause movement of the diaphragm wall 60 until the fluid supply above inlet valve 42 is nearly completely exhausted. It is also noted that preferably the diaphragm wall 60 moves between its position in which the metering chamber is empty and its position in which the metering chamber is filled with fluid without substantial resistance or without adding substantial pressure to the hydrostatic pressure of the fluid filling the metering chamber. Accordingly, the diaphragm is preferably made of a thin resilient material.

Although the volumetric capacity of metering chamber 24 may be made to vary widely depending on the quantity of fluid desired to be delivered by the apparatus in each volumetric increment and the particular application of the apparatus involved, in intravenous administration of fluid it is preferable that the metering chamber be less than one cubic centimeter. Particularly, in intravenous administration of fluids to humans, it is preferable that the volumetric capacity of the metering chamber for fluid be on the order of two tenths of a milliliter, which is received and emptied from the metering chamber as the resilient diaphragm wall 60 moves back and forth. Hence, the predetermined volumetric increment of fluid received and emptied by the metering unit during each time interval will be two tenths of a milliliter of fluid for this capacity of the apparatus. In this arrangement of the metering chamber, it is preferable to have inlet conduit 26 and outlet conduit 28 of sufficient internal cross-sectional area to permit a flow of two tenths of a milliliter of water through the conduits in five tenths of a second at a four inch hydrostatic pressure of the water flowing into the metering unit.

Figure 17:
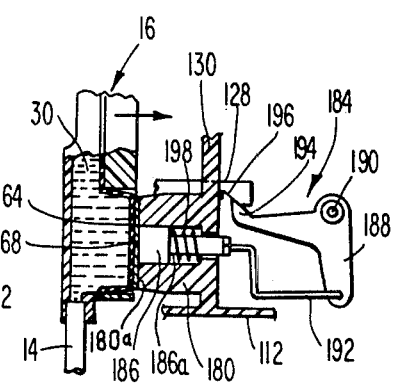
FIG. 17 is a fragmentary sectional view of a portion of the metering unit and a portion of the control unit of FIG. 16 but showing the interlock sensor mechanism of the control unit in a condition for permitting the retaining and positioning means to move the metering unit into fixed operative relationship with the control unit.

The metering unit diaphragm 38 is also provided with a resilient cup-shaped portion 64 arranged to normally extend into fluid chamber 30, as shown in FIG. 4. The cup-shaped portion 64 of diaphragm 38 is movable from its normal position to a position where the cup-shaped portion extends into cylindrical opening 66 through cover panel 36 in response to fluid filling fluid chamber 30, as when fluid is prevented from flowing through tube 14 (by a closure, not shown, at the lower end of tube 14) as shown in FIG. 17. For example, fluid is prevented from flowing through tube 14 when the apparatus is assembled and readied for operation. The cup-shaped portion 64 of the diaphragm 38 is employed with the fluid chamber 30 to provide hydraulic means cooperable with actuating means in the control unit to move fluid from the fluid chamber into the metering chamber to cause air in the metering chamber to be expelled through the inlet conduit 26. The fluid is forced from the fluid chamber when the metering unit is fastened to the control unit, as will be explained hereinafter in connection with assembling the metering unit with the control unit. A rigid plastic disc 68 is preferably bonded to the bottom surface of the cup-shaped portion 64 of diaphragm 38, as shown in FIG. 4, in order to strengthen the bottom surface of the cup-shaped portion 64.

The outlet conduit 28, which communicates between the metering chamber 24 and the fluid chamber 30, has an increased dimension portion 28a adjacent the opening to the fluid chamber. The increased dimension portion 28a, as shown clearly in FIG. 5, provides an air trap to assure that air in the fluid chamber 30 passes into the outlet conduit and hence through the metering chamber to the drip chamber 22, as fluid is forced from the fluid chamber 30 through the metering chamber, when the metering unit is being coupled into operative relationship with the control unit.

Referring to control unit 18 of FIGS. 1-3, the control unit 18 has an outer case 80 which has removable side panels 82 and 84 secured to the case as by screws 86. Case 80 of control unit 18 includes a battery compartment 88, which may contain battery 90 to provide a source of power for electrical circuitry in the control unit. Access to the battery compartment is provided through removable side panel 82. The opposite side of case 80 houses control compartment 92, which receives electro-magnetic valve actuating means or mechanism generally designated 94, shown in dot-and-dashed lines in FIG. 1, and the electronic timer means generally designated 96, which is also shown in dot-and-dashed lines in FIG. 1 as including components on a circuit board fixed to removable end panel 84.

The control unit 18 has a central receiving portion or receptacle 98 for receiving the metering unit in interfitting relationship with the control unit. The control unit receptacle 98 is provided by an opening 100 in front panel 102 of control unit case 80, opening 100 dividing front panel 102 into two sections. More particularly, opening 100 in front panel 102 has an increased dimension step portion 104 along its length adapted to receive increased dimension step portion 34a of the body portion 34 of metering unit 16 and a step portion 106 serving to close a portion of the opening 100 adjacent the area where lower end 36a of cover panel 36 of the metering unit is to be received. In this arrangement, the metering unit will pass through opening 100 in front panel 102 of control unit 18 in only one orientation of the metering unit. The top panel 108 of the control unit 18 has a generally L-shaped opening 110 with the end of one leg communicating with opening 100, and the bottom panel 112 of control unit 18 has a generally L-shaped opening 114 with the end of one leg communicating with opening 100 in the front panel. The openings 110 and 114 are in registry to complete the L-shaped control unit receptacle 98 in the control unit case 80. The control unit receptacle 98 is adapted to receive mating portions of the metering unit 16 and provides a cavity of sufficient size to permit the metering unit to be inserted into the control unit along one leg of the L-shaped receptacle to a first position in the receptacle, as shown in FIG. 15, and moved laterally along the other leg of the L-shaped receptacle into the control unit to a second position in which the metering unit is in operative relationship with the control unit as shown in FIGS. 1, 3, 9, and 14, wherein the electromagnetic valve actuating mechanism of the control unit actuates the valve means of the metering unit to control the receiving and emptying of fluid by the metering unit.

For the purpose of moving the metering unit laterally in control unit receptacle 98 from the first position to the second position to be in fixed operative relationship with the control unit, the control unit 18 is provided with manually releasable fastening means generally designated 116, which cooperates with the metering unit for fastening or holding the metering unit to the control unit. The fastening function is preferably provided by retaining and positioning means or mechanism also designated 116. The retaining and positioning mechanism 116 preferably includes a sliding carriage 118 movable between the first position shown in FIG. 15 for receiving and permitting removal of the metering unit and the second position shown in FIG. 14 for holding the metering unit in fixed operative relationship with the control unit. The sliding carriage 118 is preferably made from a piece of sheet metal and is formed with arms 120 and 122 on one side extending through openings in interior partition or rib 124 of the control case 80, the partition 124 defining the interior wall of battery compartment 88. Sliding carriage 118 also has arms 126 and 128 extending through openings in internal partition or rib 130 of control case 80, partition 130 forming the internal end wall of control compartment 92. The arms 120, 122, 126, and 128 position the sliding carriage and maintain alignment of the carriage as it moves between the first position for receiving the metering unit and the second position in which the metering unit is retained in the control unit.

For ease of movement of sliding carriage 118, arm 122 is generally U-shaped to receive a roller 132, which may be supported by a screw, between the sides of arm 122, and arms 126 and 128 cooperate with rollers 134 and 136, respectively, which may be supported by screws, in positioning and guiding movement of the sliding carriage. In order to position the metering unit 16 on sliding carriage 118 for movement with the carriage, sliding carriage 118 has a U-shaped keeper 137 with legs or projections 138 and 140 adapted to extend on opposite sides of the metering unit 16. Sliding carriage 118 also has legs 142 and 144 which extend on opposite sides of the metering unit and support the metering unit in its movement with the sliding carriage between the first position to the second position in the control unit receptacle 98.

Figure 8:
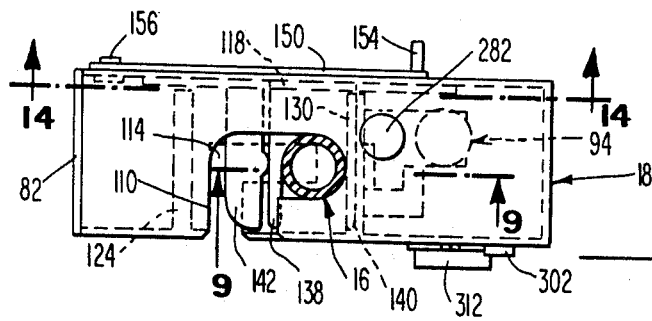
FIG. 8 is a sectional view taken along line 8—8 of FIG. 1.
Figure 14:
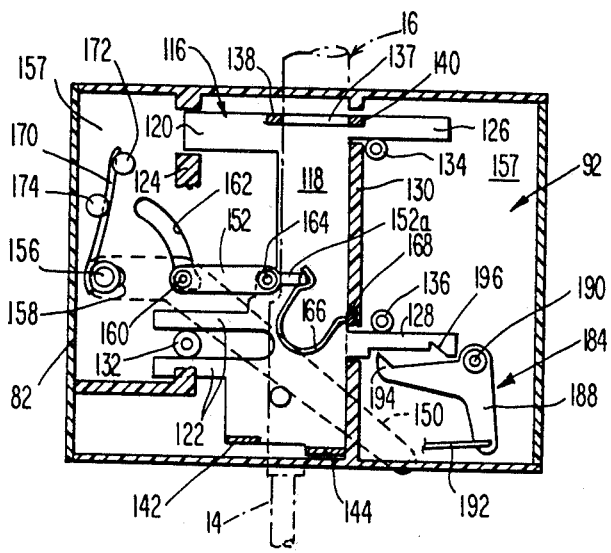
FIG. 14 is a sectional view taken along line 14—14 of FIG. 8 and showing the control unit in the condition in which the metering unit (shown in dot-and-dashed lines) is coupled to the control unit.
Figure 15:
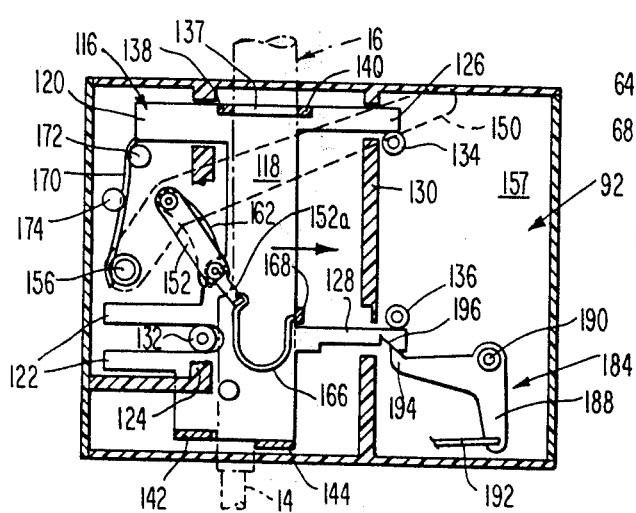
FIG. 15 is a sectional view similar to FIG. 14 but showing the retaining and positioning means of the control unit in a condition in which the metering unit (shown in dot-and-dashed lines) is released from, or received by, the control unit.

Sliding carriage 118 of retaining and positioning mechanism 116 is moved between its first position for receiving and removal of the metering unit and its second position for having the metering unit retained in fixed operative relationship with the control unit by actuating lever 150 and toggle link 152, as shown in FIGS. 8, 14, and 15. More specifically, actuating lever 150 on the outside of the back panel 157 has a finger grip projection 154 at one end and is connected at its other end to pivot stud 156 positioned in small slot 158 in back panel 157 of control unit case 80. Toggle link 152 on the inside of back panel 157 is connected to actuating link 150 by pivot pin 160 extending through arcuate slot 162 in back panel 157, arcuate slot 162 permitting movement of pivot pin 160 over the desired movement of actuating lever 150. The other end of toggle link 152 is pivotally connected to sliding carriage 118 by pivot pin 164. Toggle link 152 has an extended end portion 152a with a groove (not shown) adapted to receive one end of leaf spring 166, which has its other end positioned in a groove in flange 168 of sliding carriage 118. Leaf spring 166 is adapted to bias toggle link 152 in an over-center position of movement. Stress relief spring 170, which is held at its opposite ends by tab 172 on back panel 157 and pivot stud 156 in conjunction with biasing tab 174 formed in back panel 157, acts to bias pivot stud 156 toward the sliding carriage in slot 158 to relieve stress and provide greater tolerance in movement of the toggle retaining mechanism in cooperating with sliding carriage 118.

In operation of retaining mechanism 116, the metering unit is positioned within the control unit receptacle 98 with the retaining mechanism in the position shown in FIG. 15. After the metering unit is moved into control unit receptacle 98 abutting the sliding carriage assembly 118, actuating lever 150 is pivoted from the position shown in FIG. 15 clockwise to the position shown in FIG. 14, thereby moving sliding carriage 118 and the metering unit (shown in dot-and-dashed lines in FIGS. 14 and 15) to the position shown in FIG. 14, wherein the metering unit 16 is in fixed operative relationship with the control unit 18. It should be appreciated that the surfaces of the control unit forming the receptacle together with the legs of the sliding carriage provide alignment means for receiving the metering unit and the metering unit surfaces provide mating guides for aligning and positioning the metering unit correctly within the control unit.

Figure 16:
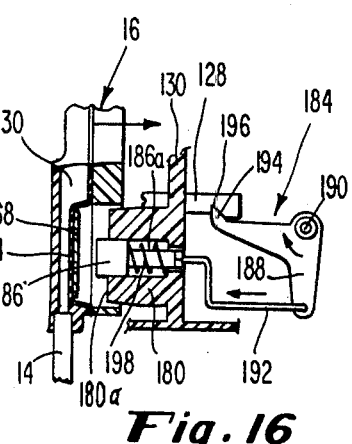
FIG. 16 is a fragmentary sectional view of a portion of the metering unit and a portion of the control unit and showing the interlock sensor mechanism of the control unit in a condition for preventing the retaining and positioning means from moving the metering unit into fixed operative relationship with the control unit.

As the retaining and positioning mechanism 116 moves the metering unit from the first position in FIG. 15 to the second position in control unit receptacle 98 shown in FIG. 14 for having the metering unit in operative relationship with the control unit, the hydraulic means, comprising cup-shaped diaphragm element 64 in fluid chamber 30 of metering unit 16, is actuated by actuating means, which is provided by ram surface 180a of hydraulic actuator boss 180 on partition 130 of control unit case 80, as shown in FIG. 9. If fluid chamber 30 of the hydraulic means is filled with fluid when the retaining and positioning mechanism moves the metering unit into fixed operative relationship with the control unit, the fluid in the fluid chamber is forced upwardly into the metering chamber by the action of ram surface 180a acting on the cup-shaped diaphragm portion 64, as shown in FIG. 17, to move diaphragm portion 64 to a position as shown in FIG. 9. This movement of fluid from the fluid chamber into the metering chamber forces air in the metering chamber to be expelled to the drip chamber 22 in the metering unit 16, which prepares the metering unit for safe operation with the control unit. In order to sense whether sufficient fluid is in the fluid chamber 30 to adequately purge air from the metering chamber 24, interlock sensor means generally designatd 184, as shown most clearly in FIGS. 16–17, is provided for sensing fluid in the fluid chamber. The interlock sensor means prevents the sliding carriage 118 of the retaining and positioning mechanism 116 from moving the metering unit into the fixed operative relationship when a sufficient volume of fluid is not present in the fluid chamber 30.

The interlock sensor means or mechanism 184 is provided by plunger 186 positioned in a central axial bore through hydraulic actuator boss 180 and extending through a reduced diameter opening in partition 130 of the control unit casing 80. Interlock sensor means 184 also includes L-shaped link 188 pivotally attached to back panel 157 of case 80 by pivot pin 190, and connecting rod 192 fixed to the plunger and pivotally attached to one end of pivoted link 188, as shown in FIGS. 16 and 17. Pivoted link 188 at its other end has a latch member or pawl 194 adapted to be received in detent 196 in arm 128 of sliding carriage 118. Pivoted link 188 is normally biased into a position to have pawl 194 engage detent 196 by helical spring 198, which surrounds a reduced diameter portion 186a of the plunger 186 and acts between the head of plunger 186 and partition 130 of the control unit case. In this arrangement, when the sliding carriage with the metering unit is moved from its first position to its second position, if sufficient fluid is present in the fluid chamber 30 to have the cup-shaped diaphragm portion 64 in opening 66 in cover panel 36 of the metering unit, as shown in FIG. 17, the plunger 186 is forced into boss 180 to move pawl 194 of link 188 to a position where detent 196 on sliding carriage 118 is not engaged by pawl 194. However, if sufficient fluid is not present in fluid chamber 30, as shown in FIG. 16, spring 198 acting on plunger 186 will cause the pivoted link 188 to be biased through rod 192 to have pawl 194 engage detent 196 to prevent sliding carriage 118 from moving the metering unit to its operative position within receptacle 98 of the control unit.

When the retaining and positioning mechanism 116 including sliding carriage 118 moves the metering unit 16 into control unit receptacle 98 to the position shown in FIG. 14, metering unit 16 is in fixed operative relationship with control unit 18 to have the valve actuator means 94 of the control unit operate the valve means 40 and 46 in the metering unit. With the metering unit fastened to the control unit, as represented in FIG. 9, the metering unit would abut against projections 200 of partition 130 to space the metering unit a slight distance from partition 130 to permit air to enter opening 62 into the metering chamber 24 enabling flexible diaphragm wall 60 to move back and forth in the metering chamber without substantial air resistance or creating a vacuum. Preferably, projections 200 formed on partition 130 of the control unit case 80 are provided by three projections spaced in a triangular manner to accurately position the metering unit adjacent partition 130 in the control unit. In addition, partition 130 is provided with two outwardly extending positioning bosses 202 and 204, which are received in mating recesses 206 and 208, respectively, of the metering unit, the bosses 202 and 204 and mating recesses 206 and 208 providing positioning and guide means for further aligning the metering unit in operative relationship with the control unit.

The electro-magnetic valve actuator mechanism 94 of the control unit comprises two electro-magnetic coil assemblies 210 and 212 wound around core member 214 and spaced apart along the core by support bracket 216, which has a recess 216a in one side adapted to receive a reduced diameter portion 214a of core 214 between the coil assemblies 210 and 212, as shown in FIGS. 9 and 11. The other side of support bracket 216 is supported in elongated slot 226 in partition 130. Coil assemblies 210 and 212 and core member 214 are further supported by brackets 218 and 220, which encircle core member 214 at opposite ends thereof to capture the coil assemblies therebetween. The brackets 218 and 220 are fixed to partition or wall 130 as by screws 222 and 224, respectively.

The magnetic circuit for the coil assemblies 210 and 212 is completed by rocker armature 230, which has leg 230a bent to extend closely adjacent end 214a of core member 214 and leg 230b bent closely adjacent end 214b of the core member. Rocker armature 230 extends through a recess 216b of support member 216 and is pivotally positioned at beveled surface 216c of support member 216 by leaf spring 232, which has one end fixed in a slot in partition 130 and its other end received in a slot in rocker armature 230 adjacent the beveled pivot surface 216c. A leaf spring 234 is provided to bias rocker armature 230 in an overcenter condition in its two extreme positions about pivot surface 216c, and leaf spring 234 is held at one end by pin 236 fixed to end 230b of rocker armature 230 and at its other end supported in a recess in bracket 220. By this arrangement, leaf spring 234 biases rocker armature 230 in the overcenter position in which leg 230a is adjacent end 214a of core member 214 or in the position in which rocker armature leg 230b is positioned adjacent end 214b of core member 214.

As rocker armature 230 moves from one extreme of its travel, such as when coil 210 is energized pulling rocker armature leg 230a adjacent the core end 214a as shown in FIG. 9, to the other extreme of its travel, such as when coil assembly 212 is energized pulling rocker armature leg 230b adjacent the core end 214b, the rocker armature moves first valve actuator pin 240 and second valve actuator pin 242 between conditions for actuating the valve elements 52 and 54, respectively, of the first and second valve means 40 and 46, respectively, of the metering unit. More specifically, valve actuator pins 240 and 242 extend through openings 244 and 246, respectively, in partition 130, the openings 244 and 246 extending through bosses 202 and 204, respectively. The valve actuator pins 240 and 242 further extend through openings in the cover panel 36 of the metering unit into the valve chambers of cavities 44 and 46, respectively, to be engagable with the diaphragm valve elements 52 and 54, respectively. The outer ends 240a and 242a of the valve actuator pins 240 and 242, respectively, have beveled surfaces to provide wedge-shaped ends to interact with the diaphragm valve elements 52 and 54, respectively, in alternately closing inlet conduit 26 and outlet conduit 28, respectively. It should be apparent that diaphragm 38 provides a seal between the body portion 34 and cover panel 36 of the metering unit so that fluid flowing through the metering unit is prevented from contacting cover panel 36, the valve actuator pins and other structure of the control unit.

The valve actuator pins 240 and 242 are actuated through their coupling to rocker armature 230, as shown most clearly in FIG. 9. More specifically, each of valve actuator pins 240 and 242 extend through rocker armature 230 and have two positioning pins 240b and 240c and 242b and 242c, respectively, extending through and axially spaced along the valve actuator pins on opposite sides of the rocker armature. Biasing springs 250 and 252 encircle valve pins 240 and 242, respectively, and have one end fixed to rocker armature 230 and their other ends abutting washers 254 and 256, respectively, which encircle the valve pins and rest against positioning pins 240c and 242c, respectively. The valve actuator pins 240 and 242 extend through openings in legs 218a and 220a of brackets 218 and 220, respectively. Guide pins 258 and 260 are fixed to bracket legs 218a and 220a and are received in axial alignment slots at the ends of valve actuator pins 240 and 242, respectively, such as alignment slot 240d of pin 240 shown in FIG. 13. The guide pins 258 and 260 maintain the alignment of the valve actuator pins 240 and 242 as the valve actuator pins move back and forth in actuating their associated valve elements.

With the metering unit 16 in operational position within the control unit 18, the coil assembly 210 may be energized to have rocker armature leg 230a drawn to the position shown in FIG. 9 adjacent core end 214a. The magnetic circuit for core assembly 210 in this instance is through core member 214, rocker armature leg 230a, and support bracket 216 to the other side of coil assembly 210. In the condition with coil 210 energized, rocker armature 230 will bias valve actuator pin 242 against diaphragm valve element 54 to close the outlet valve 46 and prevent flow of fluid through outlet conduit 28. With the inlet valve 42 open and the outlet valve 46 closed, an increment of fluid is permitted to flow into metering chamber 24 filling the metering chamber, diaphragm wall 60 being moved to the position in FIG. 9 with the metering chamber at full capacity.

When coil assembly 210 is deenergized and coil assembly 212 is energized, rocker armature end 230b will be drawn adjacent core end 214b to move valve actuator pin 240 to deform valve element 52, closing inlet valve 42 and hence inlet conduit 26. In this condition, valve actuator pin 242 does not deform diaphragm valve element 54 and flow of fluid is permitted through outlet valve 46 and hence outlet conduit 28. With the inlet valve 42 closed and the outlet valve 46 open, the increment of fluid in the metering chamber 24 will be emptied and the diaphragm wall 60 will collapse the metering chamber to be in its normal position as shown in FIG. 4. Thus, the resilient diaphragm wall 60 provides a movable wall in the metering chamber for varying the size of the metering chamber in response to fluid being received in the metering chamber and emptied from the metering chamber. This cycle of operation of the inlet and outlet valves is repeated as the coil assemblies 210 and 212 are sequentially energized to move rocker armature 230 between its extreme positions actuating valve pins 240 and 242 to alternately close the inlet and outlet valves. It should be appreciated that, when the metering unit 16 is moved into operative relationship with the control unit 18 by retaining and positioning mechanism 116, one of the valve actuator pins will be actuating its associated diaphragm valve element, such as valve actuator pin 242 actuating diaphragm valve element 54 to close the outlet valve 46 in FIG. 9. The particular valve actuator pin actuated to close its associated valve will depend upon the overcenter position of rocker armature 230 when the units are assembled together.

With the metering unit 16 and control unit 18 assembled together in operative position, it is desirable to be able to permit fluid to flow through the metering unit before the coil assemblies 210 and 212 are alternately energized. For this purpose, valve-release cam mechanism generally designated 270 is provided to move the engaged valve actuator pin from closing its associated valve element in the metering unit. More specifically, valve-release cam mechanism 270 comprises a slidable cam bar 272, as shown in FIG. 12, received in a cavity or recess 274 in partition 130 of control unit case 80. The cavity 274 is formed in a shape to permit limited longitudinal movement of the cam bar 272. The cam bar 272 may be held within cavity 274 by any suitable means, such as screws 276 and 278 having their heads extend over the cam bar in cavity 274. Cam bar 272 has tabs 272a and 272b which provide cams adapted to contact pins 240c and 242c, respectively, if the associated valve actuator pin 240 or 242, respectively, is in a position to close its associated valve.

Actuation of cam bar 272 is provided by manual depression of plunger 280, which is fixed at one end to flange 272c of the cam bar and at its other end extends through an opening in top casing panel 108 to receive push button 282. A helical spring 284 encircles the push button 282 between the head of the push button and top panel 108 to bias the push button and, hence, cam bar 272 to one extreme position of its travel in which cam bar 272 engages end 274a of cavity 274. When it is desired to open both valves in the metering unit to permit flow of fluid through the metering unit, push button 280 is manually depressed moving cam bar 272 along its path of travel to have the appropriate cam tab engage the positioning pin of the actuated valve actuator pin. For example, in the arrangement shown in FIG. 9, when push button 282 is manually depressed moving cam bar 272 along its path of travel, cam tab 272b would engage positioning pin 242b to move valve actuator pin 242 out of deforming engagement with diaphragm valve element 54. A similar movement of valve actuator pin 240 would occur, if valve actuator pin 240 was deforming its diaphragm valve element as when rocker armature 230 is in its other extreme position of movement.

Figure 20:
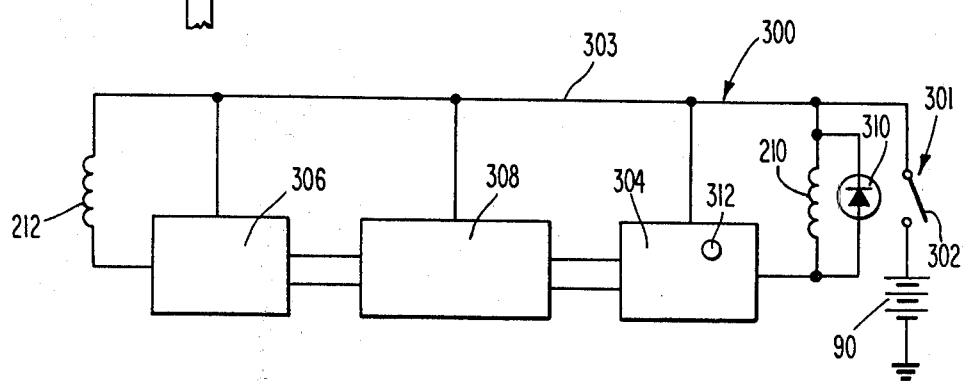
FIG. 20 is an electrical schematic diagram, partly in block form, illustrating the timer control circuit for providing time intervals during which the control unit actuates the metering unit to receive and empty fluid.

A circuit for energizing the coil assemblies 210 and 212 is schematically shown, partly in block form, in FIG. 20. The schematic diaphragm of FIG. 20 illustrates the timer means for sequentially providing a first time interval in which the inlet valve permits passage of fluid into the metering chamber for filling the metering chamber and the outlet valve is responsive to the valve actuator pin 242 of the control unit to prevent the passage of fluid and providing a second time interval in which the inlet valve is responsive to valve actuator pin 240 of the control unit to prevent passage of fluid into the metering chamber and the outlet valve permits emptying of the increment of fluid contained in the metering chamber. The first time interval and second time interval are added to provide a total time interval for a cycle of operation of the metering unit with the control unit.

In the schematic diagram of FIG. 20, battery 90, which is located in control unit battery compartment 88 as previously mentioned, has its negative terminal connected to electrical ground and its positive terminal connected to manual control switch generally designated 301 having pole or switch actuator 302, which is shown as a switch button on front panel 102 of control unit casing 80 in FIGS. 1-3. The other side of switch 301 is electrically connected to coils 210 and 212 from common electrical line 303, as shown in FIG. 20. The other sides of coils 210 and 212 are connected to first timer output circuit 304 and second timer output circuit 306, respectively. The first timer output circuit 304 and second timer output circuit 306 have switching circuit 308 connected therebetween and each of circuits 304, 306, and 308 are electrically connected to switch 301 by their connection to common electrical line 303 in FIG. 20. The function of first timer output circuit 304, second timer output circuit 306, and switching circuit 308 in timer circuit 300 is merely to provide the first time interval in which coil 210 is energized and the second time interval in which coil 212 is energized. Of course, when coil 210 is energized, coil 212 is deenergized, and vice versa. Thereafter, the cycle repeats itself with coil 210 first being energized and then deenergized and subsequently coil 212 being energized and deenergized during the different time intervals. The sum of the number of total time intervals would comprise a time period in which a desired dose or quantity of fluid would be administered to the patient.

Circuits of the type of function as set forth above to alternately energize and deenergize coils 210 and 212 are conventional in electrical circuitry and the design of this type of circuit is within the skill in the art. The schematic timer circuit 300 of FIG. 20 is merely provided to indicate one type of schematic illustration for a circuit to energize coils 210 and 212. For example, in one specific arrangement of the timer circuit for FIG. 20, first timer output circuit 304 and second timer output circuit 306 are provided by similar electrical components. First timer output circuit 304 is provided by a circuit including a programmable unijunction transistor which is rendered conductive by the charging of a capacitor and controls a circuit through the coil 210, the charging time of the capacitor being regulated by a variable resistor in the programmable unijunction transistor circuit. When the capacitor is charged to a predetermined potential the unijunction transistor is rendered conductive to cause a circuit to be completed through the coil 210, and, when the charge on the capacitor is dissipated, the unijunction transistor ceases to conduct and the circuit through coil 210 is opened to deenergize the coil 210. Such operation of the programmable unijunction transistor circuit also provides an output to switching circuit 308. A similar type of programmable unijunction transistor circuit with a variable resistor and capacitor arrangement to govern the conduction of the programmable unijunction transistor is provided for second timer output circuit 306 to control the energizing and deenergizing of coil 212 and provide an output to switching circuit 308.

With this type of programmable unijunction transistor circuit for the first and second timer output circuits, the switching circuit 308 is provided by a bistable flip-flop circuit, which provides alternating activation of the first and second timer output circuits 304 and 306. An overall manner of operation for the first and second timer output circuits in conjunction with the flip-flop circuit 308 with the components as outlined above would be as follows. When switch 301 is closed, switching circuit 308 will be in one of its stable conditions to have one of the timer output circuits begin its cycle of causing energization of its associated coil. For example, if switching circuit 308 is in the condition to have the first timer output circuit 304 begin in its cycle of operation, a capacitor is charged to a potential for rendering conductive its associated programmable unijunction transistor to cause completion of the circuit through the coil 210, thereby energizing the coil. When the first timer output circuit becomes non-conductive, current flow through coil 210 will stop. A light emitting diode 310 is shown connected across coil 210 and is operated by the voltage created by the collapsing field in coil 210 to energize the light emitting diode 310. Thus, without draining energy from the battery, diode 310 provides a light signal indicating that the control unit is operating. The light emitting diode 310 may be positioned in the front panel of the control unit casing 80, as shown in FIGS. 1-3, to provide a clearly visible indication of the operation of the control unit. When first timer output circuit 304 is actuated between its conductive and non-conductive states, a signal is provided to flip-flop circuit 308, which switches it to permit second timer output circuit 306 to operate through its cycle of conductive and non-conductive states to energize coil 212 and reset the flip-flop circuit to begin the cycle of conduction and non-conduction for the first timer output circuit. This cycle of operation continues throughout the administration of a desired dose of fluid, thereby causing the metering chamber to receive and drain the volumetric increments of fluid of a quantity predetermined by the capacity of the metering chamber 24.

In the administration of fluid to a patient, it is preferable to have the time interval for permitting the metering chamber to be drained or emptied longer than the time interval for filling the metering chamber, so that sufficient time will always be allowed to permit complete draining of the metering chamber during each drain cycle or interval irrespective of the several variables which affect the rate of flow of fluid from the metering chamber. The time intervals for operation of the inlet and outlet valves may be set at different lengths by adjusting the variable resistors which regulate the charging of the capacitors in the first and second timer output circuits 304 and 306. In the preferred arrangement of the apparatus, the time interval for the inlet valve being open for filling the metering unit would remain constant and need not be varied in use of the apparatus in controlling the intravenous administration of fluids. In order to facilitate variations in time for the outlet valve to be opened, a control dial 312 for controlling the resistance of the variable resistor in the first timer output circuit 304 is provided. In this manner, the time for energizing coil 210 and, hence, closing the outlet valve is varied. The dial 312 varying the time interval of operation of the first timer output circuit 306 is provided on front panel 102 of control unit case 80, as shown in FIGS. 1-3, and is calibrated in milliliters per minute for ease of use of the apparatus. For example, dial 312 may be calibrated from two tenths milliliters per minute of administration of fluid to ten milliliters per minute of administration of fluid to provide a gradation in rate of administration of fluid by the apparatus. For each administration of a dose of fluid to a patient, dial 312 would be set to a desired flow rate of the fluid.

In the setup of the apparatus in accordance with the present invention to administer a prescribed dose of fluid to a patient, the metering unit 16 is connected to tube 14. A cap (not shown) normally provides closure of the other end of outlet tube 14 and is subsequently removed for connection of the hypodermic needle to tube 14. Conduit means 20 of the metering unit 16 is plugged into standard dose container or bottle 12, containing the prescribed dose of fluid to be administered. Container 12 is then suspended in an inverted position with the metering unit connected thereto above the level of the patient to whom the dose is to be administered so that fluid will drain through the metering unit by gravity flow and so that the metering chamber is permitted to drain completely during each drain interval. For a patient confined to bed, the metering unit should be positioned at a level about thirty inches or more above the patient. This arrangement provides a sufficient pressure differential between the level of fluid in the metering chamber and the venous pressure of the patient to overcome the venous back pressure of the patient and allow complete emptying of the metering chamber during each drain interval. Also, the pressure of the fluid flowing from the container by gravity flow provides the fluid at a hydrostatic pressure to properly operate the filling of the metering chamber.

In this orientation of the fluid container 12 and metering unit 16, fluid will flow by gravity down into the metering unit, which will subsequently be coupled to the control unit, through the inlet valve to partially fill the metering chamber by moving diaphragm wall 60 under the pressure of the fluid. The fluid will also pass from the metering chamber through the outlet valve into the fluid chamber, thereby moving cupshaped dome 64 of the diaphragm under the pressure of the fluid to increase the capacity of fluid chamber 30, as when cup-shaped diaphragm portion 64 is in the position shown in FIG. 17. The fluid in passing through the metering unit 16, as described above, will also generally flow a distance into the top of outlet tube 14 before the pressure of air will restrain the fluid flow. It should be appreciated that the fluid flowing through the metering unit as described will drip through the reservoir or drip chamber 22 without filling the drip chamber or causing a reservoir of fluid in the drip chamber due to the air captured therein.

The control unit 18 is next coupled to the metering unit by inserting the metering unit into control unit receptacle 98 within the legs of sliding carriage 118, as when the retaining and positioning mechanism 116 of the control unit 18 is in the position shown in FIG. 15 with the metering unit being indicated in dot-and-dashed lines. As previously mentioned, the surfaces defining the control unit receptacle and the metering unit are provided such that the metering unit fits within the control unit receptacle 98 in only one orientation. The actuating lever 150 of the fastening or retaining mechanism 116 is moved in a clockwise direction, as shown in FIG. 15, to move the sliding carriage and, hence, the metering unit into operative relationship with the control unit, in which condition the metering unit is adjacent partition 130 of the control unit so that valve actuator pins 240 and 242 may open and close the inlet and outlet valves of the metering unit when the electro-magnetic mechanism 94 is energized. It should be appreciated that, with fluid in the fluid chamber, cup-shaped diaphragm portion 64 actuates the plunger 186 of interlock sensor means 148 to permit detent 196 of sliding carriage 118 to move free of pawl 194 to the second position of the sliding carriage shown in FIG. 14.

As the metering unit 16 is moved into fixed operative relationship with the control unit, the hydraulic actuator moves cup-shaped diaphragm portion 64 into its normal position, thereby forcing fluid from the fluid chamber 30 into metering chamber 24 and drip chamber 22. This forcing of fluid from the fluid chamber into the metering chamber purges air from the metering chamber and communicating conduits and partially fills the reservoir or drip chamber 22 with fluid. To purge air from the outlet tube 14, the cap (not shown) on the tube 14 is removed and valve release cam mechanism 270 is actuated by briefly depressing push button 282 to cause both the inlet and outlet valves to be opened to permit fluid to flow through the metering unit and tube 14. With tube 14 filled with fluid, the hypodermic needle is connected to the tube in a conventional manner, the hypodermic needle being inserted into the vascular system of the patient.

The apparatus is set to a desired flow rate of the fluid by rotating dial 312 to the desired point as indicated on the calibration scale on the front panel. The setting of dial 312 is translated into a desired rate of administration of each volumetric increment of fluid held by the metering chamber by varying the time interval that the outlet valve remains open for emptying of the predetermined increment of fluid from the metering chamber. Initiation of the administration of fluid is begun by actuating switch button 302 to its "ON" position, moving the switch pole 302 to close switch 301 in timer circuit 300. The operation of timer circuit 300 recycles the electromagnetic valve actuating mechanism to cause the filling and emptying of the metering chamber once during each cycle of operation of opening and closing the inlet and outlet valves of the metering unit. As previously mentioned, during each cycle of operation of the timer circuit, the inlet valve would be open to permit filling of the metering chamber to capacity with diaphragm wall 60 abutting metering chamber surface 24b and then the inlet valve would be closed and the outlet valve open so that fluid flows by gravity from the metering chamber to the patient emptying the metering chamber before another cycle of operation. Hence, the inlet valve and outlet valve are alternately opened and closed during each time interval, as rocker armature 230 moves from one of its extreme positions to the other. However, it should be appreciated that when rocker armature 230 passes through its neutral position, both the inlet valve and outlet valve are closed by the valve actuator pins 240 and 242, respectively, so that at no time are both valves open when the metering unit is fastened in operative relationship with the control unit.

Normally, the termination of administration of a dose is accomplished by the removal of the hypodermic needle from the patient immediately upon completion of administration of the prescribed volume of fluid and while fluid is still flowing through the hypodermic needle or immediately after flow of fluid is stopped. The container containing the prescribed dose usually contains a quantity of fluid beyond the prescribed dose for safety in preventing the stoppage of flow of fluid immediately upon a prescribed dose being administered.

In accordance with the present invention, as hydrostatic pressure in the supply source container decreases due to the level of fluid being lowered some distance below the level where the prescribed dose has been administered (or the fluid source container has been drained below a predetermined level), the volume of fluid in each increment passing through the metering chamber will automatically be gradually reduced. For example, when fluid only remains in the reservoir or drip chamber 22, which has the fluid at a lower or second hydrostatic pressure than that provided by the fluid in supply container 12, fluid will only fill the metering chamber to a reduced volume during the time intervals when the outlet valve is closed and the inlet valve is open in the metering unit because the pressure of the fluid is not sufficient to cause fluid to flow into the metering chamber fast enough to fill the metering chamber to capacity within the time interval provided.

It will also be appreciated that the fluid level at which the reduction in the size of the volumetric increments of fluid in the metering chamber occurs after the desired dose has been administered will be affected by the viscosity of the fluid being administered. Nevertheless, the apparatus will operate at a reduced rate of fluid administration to protect the patient and permit a longer time period for the hypodermic needle to be removed from the patient by the doctor or nurse without serious adverse consequences to the patient. It will further be appreciated that, even after there is insufficient fluid above the inlet valve to cause movement of the diaphragm wall in the metering chamber, air will not pass through the metering chamber due to an inherent tendency of the diaphragm wall 60 to act as a shutoff valve when the hydrostatic pressure in the part of the drainage system directly below the metering chamber is below atmospheric pressure.

Figure 18:
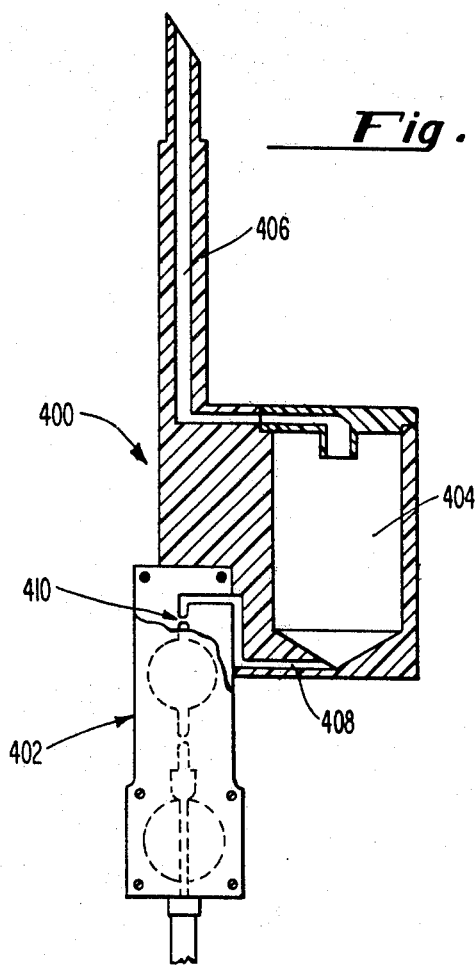
FIG. 18 is a fragmentary sectional view of an alternative embodiment of a metering unit which may be employed in accordance with the present invention.
Figure 19:
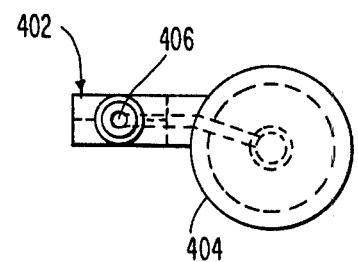
FIG. 19 is a plan view of the metering unit of FIG. 18.

It should be understood that many modifications may be made in the arrangement of the apparatus in accordance with the present invention while still employing the concept of the invention. A modified embodiment of the metering unit is shown, for example, in FIGS. 18 and 19. In the embodiment shown in FIGS. 18 and 19, the metering unit has been modified to provide greater effectiveness of the automatic slowing down of the rate of administration of fluid through the metering unit after a prescribed dose has been administered. The primary difference in structure of the metering unit of FIGS. 18 and 19 and that of FIGS. 1-4 lies in the change in size and location of the reservoir or drip chamber. Metering unit 400 in FIGS. 18 and 19 has a metering unit body 402 which is identical to the metering unit body of the metering unit of FIG. 4 in the provision of the inlet valve, metering chamber, outlet valve, and fluid chamber arrangements. The metering unit 400 has its reservoir or drip chamber 404 offset, lowered, and enlarged from the location in FIG. 4. Drip chamber 404 is enlarged for increased capacity to provide a greater reservoir supply for fluid, and the drip chamber is offset and lowered with respect to the inlet valve in the metering chamber in order for the drip chamber to supply the last few cubic centimeters of fluid to the metering chamber at a very low hydrostatic pressure as the fluid drains from the drip chamber into inlet conduit 408. Inlet conduit 408 is shaped to have the fluid flow upwardly along a vertical path before proceeding downwardly through the metering unit inlet valve generally designated 110 to the metering chamber. Also, in FIG. 18, the length of inlet passage 406 is increased in order to provide a sufficient hydrostatic pressure above the metering chamber for reliable operation with a very short time interval for filling the metering chamber. In this arrangement, the rate of administration of fluid through the metering unit will decrease significantly before the fluid level in passage 406 is exhausted and will decrease to a minute fraction of the selected rate of administration before stopping completely. In use of the metering unit of FIGS. 18 and 19, the receptacle of the control unit, such as shown in FIG. 3, would have to be enlarged and modified in order to accommodate the enlarged and offset drip chamber portion of the modified metering unit as would be obvious to those skilled in the art. It should also be understood that the drip chamber illustrated in FIG. 18 could be considered a lower extension of the supply container for the purpose of accomplishing the automatic reduction in rate of fluid administration of this invention and the reservoir or drip chamber need not be integrally attached to the body of the metering unit as part of the metering unit. For example, the reservoir chamber might be connected to the metering unit by a flexible tube.

It should be appreciated that provision may be made in the apparatus for means to vary the size of the metering chamber, depending on the desired quantity of fluid to be delivered in each increment received and dispensed by the metering chamber. An adjustable member could be provided from the control unit extending through opening 62 of the metering unit into the metering chamber to vary the stroke of the diaphragm wall 60 in filling the metering chamber with the desired increment of fluid. Further, many different electro-magnetic valve actuator arrangements may be provided besides the specific toggle rocker armature arrangement disclosed. Electronic circuitry could be provided to independently actuate each valve element to open and close the inlet and outlet valves in the metering unit. Moreover, in many applications of the metering apparatus, the drip chamber may be omitted from the apparatus, and the fluid chamber and associated interlock sensor mechanism may be omitted. Furthermore, the fastening means for holding the metering unit and control unit together in fixed operative relationship could be provided as part of the metering unit, if desired.

It will be observed that in accordance with the present invention, an improved apparatus is provided for controlling the dispensing of fluid that is light in weight, easily portable and rugged in design. The metering unit is the only portion of the apparatus which needs to be maintained in a sterile condition, and the metering unit is provided as an inexpensive, disposable item that is replaced after each use of the apparatus. It will also be appreciated by those skilled in the art that the capabilities of the apparatus described fulfill the need for a safe intravenous administration device that is useful in a wide variety of applications for accurately controlling the rate of flow of fluid.

While the invention has been described with particular reference to specific embodiments thereof in the interest of complete definiteness, it may be embodied in a large variety of forms diverse from the ones specifically shown and described without departing from the scope and spirit of the invention as defined by the appended claims.

We claim:

1. A disposable metering unit for use in controlling the intravenous administration of a fluid to a patient, comprising:

inlet conduit means for delivering fluid at a hydrostatic pressure from a source of fluid; metering means for receiving a predetermined increment of fluid from the conduit means and for emptying the predetermined increment of fluid by the suction of gravity flow without adding substantial pressure to the hydrostatic pressure, said metering means defining a metering chamber having opposed inner walls, and movable diaphragm means positioned in the metering chamber, said diaphragm means being capable of being moved at the hydrostatic pressure between a first position in which said diaphragm means is positioned against one of the opposed inner walls of the metering chamber with substantially all of the volume of the chamber being on one side of the diaphragm means, and a second position in which the diaphragm is in contact with the other of said opposed inner walls of the metering chamber with substantially all of the volume of said metering chamber being on the other side of said diaphragm means, whereby said metering means may be repeatedly filled with fluid to impel the diaphragm means into its second position and then to drain said fluid from the metering means with the diaphragm means moving to the first position, whereby said predetermined increments of fluid may be of constant volume and may be passed through said metering means; and outlet conduit means communicating with the metering means for receiving said increments wherein gravity suction flow takes place to empty the metering means when the outlet means is opened, both said inlet and outlet conduit means communicating with the metering chamber at the same side of said diaphragm means, said metering means defining exterior vent means communicating into said metering chamber adjacent the opposed inner wall of said metering chamber with which the diaphragm is in contact in its second position, to facilitate free flow of air into and out of said metering chamber as said diaphragm means moves between its first and second positions;

and means for permitting the alternative and sequential valving of fluid through said inlet conduit means and outlet conduit means.

2. The disposable metering unit of claim 1 in which a projection is positioned on the inner wall of each inlet and outlet conduit means in opposed relation to apertures in said walls to serve as part of said valve means.

3. The metering unit of claim 1 in which the unit includes a rigid body portion and a cover portion with a cavity formed in the unit to provide the metering chamber, the size of the cavity determining the capacity for the predetermined increments of fluid.

4. The metering unit of claim 1 in which the movable diaphragm means is resilient to conform to the shape of the cavity.

5. The metering unit of claim 1 in which the unit includes a rigid body portion and a cover portion with an arcuate-shaped cavity formed in the body portion and a communicating arcuate-shaped cavity formed in the cover portion to provide the metering chamber.

6. The metering unit of claim 5 in which said diaphragm has an arcuate-shaped portion which conforms to the arcuate-shaped cavity of one of the body and cover portions.

7. The metering unit of claim 1 in which the metering chamber has a volumetric capacity of less than one cubic centimeter.

8. The metering unit of claim 7 in which the valve means is actuated to provide the predetermined rate of administration of fluid in the range of two tenths milliliter per minute to ten milliliters per minute.

9. The metering unit of claim 1 further including hydraulic means with a fluid chamber receiving fluid from the metering chamber for having fluid in the fluid chamber moved into the metering chamber to cause air in the metering chamber to be expelled through the inlet conduit means when the metering unit is in operative relationship.

10. The metering unit of claim 1 further including a reservoir chamber adapted to receive a portion of the increments of fluid from the source at a first hydrostatic pressure and to hold the fluid at a second hydrostatic pressure, the metering chamber receiving the predetermined increment of fluid from the reservoir chamber and emptying the predetermined increment of fluid without adding substantial pressure to the second hydrostatic pressure.

11. The metering unit of claim 10 in which means is provided for supporting the reservoir chamber with respect to the metering chamber so that when the source of fluid has been drained below a predetermined level, the second hydrostatic pressure of the fluid in the reservoir chamber is only sufficient to have the metering chamber receive a portion of a predetermined increment of fluid from the reservoir chamber to be emptied from the metering chamber.

12. A disposable metering unit for use in controlling the intravenous administration of a fluid to a patient, comprising:

inlet conduit means for delivering fluid at a hydrostatic pressure from a source of fluid;

metering means for receiving a predetermined increment of fluid from the conduit means and for emptying the predetermined increment of fluid by the suction of gravity flow without adding substantial pressure to the hydrostatic pressure, said metering means defining a metering chamber having opposed inner walls, and movable diaphragm means positioned in the metering chamber, said diaphragm means being capable of being moved at said hydrostatic pressure between a first position in which said diaphragm means is positioned against one of the opposed inner walls of the metering chamber with substantially all of the volume of the chamber being on one side of the diaphragm means, and a second position in which the diaphragm is in contact with the other of said opposed inner walls of the metering chamber with substantially all of the volume of said metering chamber being on the other side of said diaphragm means, whereby said metering means may be repeatedly filled with fluid to impel the diaphragm means into its second position and then to drain said fluid from the metering means with the diaphragm means moving to the first position, whereby said predetermined increments of fluid may be of constant volume and may be passed through said metering means;

outlet conduit means communicating with the metering means for receiving said increments wherein gravity suction flow takes place to empty the metering means when the outlet means is opened, the transverse dimensions of said inlet and outlet conduit means being substantially less than the transverse dimension of said metering means, said diaphragm means defining extensions residing in said inlet and outlet conduit means; both said inlet and outlet conduit means communicating with the metering chamber at the same side of said diaphragm means, said metering means defining exterior vent means communicating into said metering chamber adjacent the opposed inner wall of said metering chamber with which the diaphragm is in contact in its second position, to facilitate free flow of air into and out of said metering chamber as said diaphragm means moves between its first and second positions; and apertures positioned in said inlet conduit means and outlet conduit means adapted to permit passage of plunger means respectively into said inlet and outlet conduit means to respectively press said diaphragm extensions into sealing relationship with walls of the inlet and outlet conduit means, to selectively block liquid flow through said inlet and outlet conduit means.

13. The disposable metering unit of claim 12 in which a projection is positioned on the inner wall of each inlet and outlet conduit means in opposed relation to said apertures, to define a valve face against which said diaphragm extensions are pressed by said plunger means.

14. A disposable metering unit for use in controlling the intravenous administration of fluid to a patient, comprising:

(a) a reservoir chamber adapted to receive a portion of the increments of fluid from a source of fluid at a first hydrostatic pressure, and to hold the fluid at a second hydrostatic pressure;

(b) a metering chamber for receiving a predetermined increment of fluid from said reservoir chamber and for emptying the predetermined increment of fluid without adding substantial pressure to the second hydrostatic pressure, said metering chamber having a movable diaphragm means therein to meter a predetermined quantity of fluid therethrough;

(c) conduit means for delivering fluid at the source of fluid having a supply of predetermined increments of fluid to the metering chamber; and (d) valve means actuatable for regulating the receiving and emptying of each of the predetermined increments of fluid by the metering chamber to be administered to the patient at a predetermined rate of administration.

15. The metering unit of claim 14 in which means is provided for supporting the reservoir chamber with respect to the metering chamber so that when the source of fluid has been drained below a predetermined level, the second hydrostatic pressure of the fluid in the reservoir chamber is only sufficient to have the metering chamber receive a portion of a predetermined increment of fluid from the reservoir chamber to be emptied from the metering chamber.

16. Apparatus for controlling the intravenous administration of fluid to a patient which comprises:

inlet conduit means for delivering fluid at a hydrostatic pressure from a source of fluid;

metering means for receiving a predetermined increment of fluid from the conduit means and for emptying the predetermined increment of fluid by the suction of gravity flow without adding substantial pressure to the hydrostatic pressure, said metering means defining a metering chamber having opposed inner walls, and movable diaphragm means positioned in the metering chamber, said diaphragm means capable of being moved at the hydrostatic pressure between a first position in which said diaphragm means is positioned against one of the opposed inner walls of the metering chamber with substantially all of the volume of the chamber being on one side of the diaphragm and a second position in which the diaphragm is in contact with the other of said opposed inner walls of the metering chamber with substantially all of the volume of said metering chamber being on the other side of said diaphragm means, whereby said metering chamber may be repeatedly filled with fluid to impel the diaphragm means into its second position and then to drain said fluid from the metering means with the diaphragm means moving to the first position, whereby said predetermined increments of fluid may be of constant volume and may be passed through said metering means, both said inlet and outlet conduit means communicating with the metering chamber at the same side of said diaphragm means, said metering means defining exterior vent means communicating into said metering chamber adjacent the opposed inner wall of said metering chamber with which the diaphragm is in contact in its second position, to facilitate free flow of air into and out of said metering chamber as said diaphragm means moves between its first and second positions; and outlet conduit means communicating with the metering means for receiving said increments and conveying them to a patient wherein gravity suction flow takes place to empty the metering means when the outlet means is opened, and valve means in said inlet and outlet conduit means for the alternative and sequential valving of fluid through said inlet conduit means and outlet conduit means.

17. The apparatus of claim 16 in which the transverse dimensions of said inlet and outlet conduit means are substantially less than the transverse dimension of said metering means, said diaphragm means defining extensions residing in said inlet and outlet conduit means, apertures positioned in said inlet conduit means and outlet conduit means, and plunger means adapted to pass respectively into said inlet and outlet conduit means through said apertures to respectively press said diaphragm extensions into sealing relationship with walls of the inlet and outlet conduit means, to selectively block liquid flow through said inlet and outlet conduit means.

18. The apparatus of claim 17 in which a projection is positioned on the inner wall of each inlet and outlet conduit means in opposed relationship to said apertures, to define a valve face against which said diaphragm extensions are pressed by said plunger means.

* * * * *

UNITED STATES PATENT AND TRADEMARK OFFICE
CERTIFICATE OF CORRECTION

PATENT NO. : 4,261,356
DATED : April 14, 1981
INVENTOR(S) : Roger S. Turner and Charles R. Turner It is certified that error appears in the above-identified patent and that said Letters Patent are hereby corrected as shown below:

After the entry identifying the inventors on page 1, delete:

"Assignee: Baxter Travenol Laboratories, Inc., Deerfield, Ill."

Signed and Sealed this

Fourth Day of August 1981

[SEAL]

Attest:

GERALD J. MOSSINGHOFF

Attesting Officer — Commissioner of Patents and Trademarks